United States Patent [19]

Kishimoto et al.

[11] Patent Number: 5,473,097

[45] Date of Patent: Dec. 5, 1995

[54] GRANULES OF α-L-ASPARTYL-L-PHENYLALANINE METHYL ESTER

[75] Inventors: Shinichi Kishimoto; Akihiko Yasaki, both of Kawasaki, Japan

[73] Assignee: Ajinomoto Company, Inc., Tokyo, Japan

[21] Appl. No.: 130,534

[22] Filed: Oct. 1, 1993

Related U.S. Application Data

[63] Continuation of Ser. No. 985,931, Dec. 4, 1992, abandoned, which is a continuation-in-part of Ser. No. 886,082, May 21, 1992, abandoned.

[30] Foreign Application Priority Data

May 24, 1991 [JP] Japan .................................. 3-222525

[51] Int. Cl.$^6$ .................................................. C07C 229/00
[52] U.S. Cl. .............................................. 560/41; 426/110
[58] Field of Search ............................ 206/819; 560/41; 426/106, 110, 112, 115

[56] References Cited

U.S. PATENT DOCUMENTS

| | | |
|---|---|---|
| 3,492,131 | 1/1970 | Schlatter . |
| 3,642,491 | 2/1972 | Schlatter . |
| 4,517,214 | 5/1985 | Shoaf et al. ............................ 426/548 |
| 4,594,252 | 6/1986 | Niemczyk ............................... 426/307 |
| 4,608,263 | 8/1986 | Bergin et al. ........................... 426/303 |
| 4,810,818 | 3/1989 | Wakamatsu et al. ..................... 560/41 |
| 4,831,180 | 5/1989 | Wakamatsu et al. ..................... 560/41 |
| 4,994,605 | 2/1991 | Kishimoto et al. ..................... 562/445 |
| 5,041,607 | 8/1991 | Naruse et al. .......................... 560/41 |
| 5,097,060 | 3/1992 | Naruse et al. .......................... 560/41 |

FOREIGN PATENT DOCUMENTS

| | | |
|---|---|---|
| 0458750 | 11/1991 | European Pat. Off. . |
| 0256513 | 2/1988 | Japan ..................................... 560/41 |
| 0256515 | 2/1988 | Japan ..................................... 560/41 |
| 0256517 | 2/1988 | Japan ..................................... 560/41 |

OTHER PUBLICATIONS

Chemical Abstracts, 113, (1990), No. 130927v, Y. Shiokawa et al, "Crystal Structure of Aspartame, A Peptide Sweetener".

Chemical Abstracts, 103, (1985), No. 22917b, M. Hatada et al, "Crystal Structure of Aspartame, A Peptide Sweetener".

Chemical Abstracts, 82, (1975), No. 42000y, J. H. Berg et al, "Acid Solubilizers for Aspartyl Dipeptide Sweeteners".

Chemical Abstracts, 87, (1977), No. 83376x, M. Hatada et al, "Crystal Structure of Aspartame, A Peptide Sweetener".

*Primary Examiner*—José G. Dees
*Assistant Examiner*—Samuel Barts
*Attorney, Agent, or Firm*—Oblon, Spivak, McClelland, Maier, & Neustadt

[57] ABSTRACT

Granules of α-L-aspartyl-L-phenylalanine methyl ester, containing IB crystals of the ester and having a grain size of from 100 to 1400 μm have improved water solubility.

31 Claims, No Drawings

GRANULES OF α-L-ASPARTYL-L-PHENYLALANINE METHYL ESTER

This application is a continuation of application Ser. No. 07/985,931, filed Dec. 4, 1992, now abandoned, which is a Continuation-in-Part of application Ser. No. 07/886,082, filed May 21, 1992, now abandoned.

BACKGROUND OF THE INVENTION

1. Field of the Invention

The present invention relates to granules of α-L-aspartyl-L-phenylalanine methyl ester (α-APM) having improved water-solubility. The granules of the present invention may be packaged to protect the granules from destruction or damage during transportation or storage and to allow direct use of the granules as a sweetener.

2. Discussion of the Background

α-APM is a dipeptide sweetener having a sweetness of about 200 times that of sucrose (cane sugar). Because of its extreme sweeteners and the low calory content, it is widely used as a diet sweetener, and the worldwide demand for it is estimated to be over 10,000 tons by 1995.

Since α-APM is an added sweetener which has little bitterness or bad aftertaste, in contrast to other high-sweetness sweeteners, it is widely used and popularized as a low-calory sweetener. However, one drawback is often pointed out, i.e., that the dispersibility and solubility in water is poor. Therefore, in order to obtain α-APM having excellent solubility, various investigations for granulating or foaming and tableting it have been made by adding a vehicle or disintegrator thereto.

However, incorporation of a vehicle into α-APM is often problematic for particular uses. Therefore, high-purity and high-solubility α-APM is greatly desired.

As an attempt to improve the solubility of α-APM while maintaining high purity, a method of spray-drying a slurry of α-APM is known (Japanese Patent Publication 58-20558). A method of granulating α-APM, to which water has been added to a specified water content is also known (Japanese Patent Application Laid-Open No. 59-95862).

On the other hand, processes for producing α-APM crystals are known to produce various crystal forms (European Patent 0119837). Of these crystal forms, IB crystals have a higher solubility than IIA crystals and IIB crystals, as dry crystals.

However, IB form crystals of α-APM are known to still contain crystals having low solubility. For example, crystal characteristics, i.e., whether bundle-like crystals form or needle-like crystals form, causes noticeable differences in the dispersibility and solubility of crystals in water. The bundle-like crystals have a higher dispersibility and solubility in water than the needle-like crystals.

IB needle-like crystals often require a long time for dispersing or dissolving them into water, which is almost comparable to IIA crystals or IIB crystals, depending upon the crystallization and drying conditions employed in preparing them.

The term "needle-like crystals", as referred to herein, indicate those crystals which are obtained by cooling crystallization under ordinary stirring conditions without a pseudo-solid phase.

The term "bundle-like crystals", as referred to herein with respect to crystal behavior, indicate those crystals which are obtained by cooling crystallization of an α-APM solution with no stirring condition via its pseudo-solid phase, as described in Japanese Patent Publication No. 2-45638 (crystallization of α-APM). When these crystals are observed with a scanning electron microscope (SEM) under magnification, they are found to be crystal aggregates where a plurality of needle-like crystals are bundled together to seemingly form one crystal.

SUMMARY OF THE INVENTION

The object of the present invention is to improve the solubility of the above-mentioned IB crystals of α-APM having a poor solubility to such a degree that the time necessary for dissolving these crystals is half or less of the time necessary for dissolving the original powder of the compound.

Another object of the invention is to provide a packaged form of the improved granules of the present invention suitable for direct use of the improved granules as a sweetener without further modification.

These and other objects which will become apparent in the course of the following descriptions of exemplary embodiments have been achieved by the present process in which the solubility of IB crystals of α-APM is improved by granulating the crystals to a grain size of 100–1400 microns.

DETAILED DESCRIPTION OF THE PREFERRED EMBODIMENTS

It has now been discovered that the solubility of IB needle-like crystals of α-APM is improved by granulating the crystals to grains having a particular grain size.

A binder is used for granulating and shaping the α-APM crystals. One or more binders such as water and aqueous solutions of alcohols, saccharides and inorganic materials such as lactose, lactose anhydride, dextrin, gelatin, soluble starch, sucrose, sorbitol, etc, may be used as the binder.

Granulation of α-APM may be effected by any known method of mixing granulation, powder compression granulation, extrusion granulation, fluidizing granulation, rolling granulation, pulverizing granulation and others. From the viewpoint of low heat load and for the purpose of avoiding complicated processing, dry granulation such as powder compression granulation is industrially preferred.

The magnitude of the effect of the present invention depends upon the content of IB crystals in the granulated α-APM product. When the content of IB crystals is large, the product must be granulated to a relatively narrow grain size range. However, when the content of IB crystals is low, the effect of the present invention is seen over a much broader grain size range.

The grain size of the granulated product containing a high amount of IB crystals, i.e. an amount of 90 wt. % or more, must be within the range of from 100 to 500 μm, preferably from 150 to 300 μm.

If the grain size is less than 100 μm, the water-dispersibility of the granules is poor and dissolution of the granules requires long times. On the other hand, if the grain size is more than 500 μm, the contact area between water and grains is unfavorably decreased so that improvement of the water-solubility of the grains can not be attained and the time necessary for dissolution in water can not be reduced to half or less of the time necessary for dissolving the original powder of the compound.

Therefore, the size of the granulated product is from 100 to 500 μm. Where the size of the granulated product falls within this range, the time necessary for dissolving the granulated low-solubility IB crystals of α-APM in water is reduced to about half or less of the time necessary for dissolving the original powder of the compound.

As used herein, the term "original powder" means the α-APM which is used as the starting material for the present process, prior to granulation. Such starting original powders will generally have an average particle size of 50–60 microns or less. The original powder may be produced by cooling crystallization with stirring and pulverizing into a powder having the described particle size after drying.

When the content of IB crystals is low, i.e., less than 10 wt % in the α-APM to be granulated, the solubility of the original α-APM powder itself is low. Therefore, the improvement in the solubility of the granulated product obtained from it is achieved over a broad range of grain sizes. That is, the grain size of the granulated product may be within the range of from 100 to 1400 μm, preferably from 150 to 500 μm. When the grain size is within this defined range, the time necessary for dissolving the granulated product in water is reduced to about half or less of the time necessary for dissolving the original powder of the compound, i.e., a high-purity α-APM product.

In accordance with the present invention, even low-solubility powdery α-APM containing IB crystals can be formed into granules having an improved solubility in water. When the granules of α-APM of the present invention are added to drink or other products, the time necessary for dissolving them is reduced and the distribution of the operation time for dissolution is also be reduced. As a result, the granules of α-APM of the present invention may be handled with high efficiency.

The granulated product of the present invention may be directly added to food stuffs as a sweetener without further modification. Generally, the granules are packaged to protect the granules from deterioration and destruction during transportation and storage. The packing materials and package forms used to package the granules of the present invention are not limited and may include any packaging materials and package forms which are suitable for packaging foodstuffs. In a preferred embodiment, the package can be directly opened for dispensing the granules, for example, into a beverage or other food product.

Preferably, the granules are packed in a flexible bag which may be a single walled bag, a double walled or triple walled bag, etc. The flexible bag is sealed to preserve the granules, but can be opened by the user to dispense the granules as a sweetener. The flexible bag may be made from any plastic, paper, plastic-coated paper, aluminum foil, aluminum foil-coated paper, aluminum foil-coated plastic, etc. suitable for packaging foodstuffs. Such packaging materials are well known in the art and described, for example, in Kirk-Othmer, Encyclopedia of Chemical Technology, volume 11, pages 181–182, John Wiley & Sons, New York, 1980. Examples of suitable materials which can be used in the flexible bag include polyethylene, nylon, polyethylene laminated with aluminum foil, paper, polyethylene coated paper and polyethylene/paper/poly(ethylene-vinyl acetate). The flexible packages may be sealed against moisture and gas permeation using known sealing techniques and equipment.

Multiple flexible bags may be packaged into a solid walled package for shipping and storage purposes. Suitable solid packages include paper drums and boxes, metal drums and boxes, plastic drums and boxes, glass bottles, wooden boxes, etc. Typically, a desiccant, such as silica gel, is included in the solid package to minimize water vapor within the package.

The granules of the present invention can be dispensed directly from the flexible bag packaging for use as a sweetener. The granules dissolve rapidly in drinks and other products and have improved solubility.

Other features of the invention will become apparent in the course of the following descriptions of exemplary embodiments which are given for illustration of the invention and are not intended to be limiting thereof.

EXAMPLE

Sample A

A powder of α-APM was prepared in accordance with the method mentioned below as a sample for evaluation.

An aqueous α-APM solution was crystallized by ordinary cooling crystallization, where the solution was stirred (stirring crystallization not forming a pseudo-solid phase). By centrifugation, wet α-APM crystals having a water content of 60 wt. % were obtained, and were dried in a small fluidizing drier at 90° C. for 30 minutes. Then, they were milled in a small centrifugal mill (5000 rpm, using 1 mm screen) to obtain an original IB needle-like crystal powder which was identified as sample A.

Sample B 380 ml of an aqueous solution containing 17.7 kg of α-APM dissolved therein (55° C., initial concentration of α-APM 4.4 wt. %) was placed in a cooling jacketed stainless steel crystallizer having a diameter of 400 mm and having a cooling plate on the inside thereof, and a coolant at 0° C. was circulated into the cooling jacket and the cooling plate whereby the content in the crystallizer was cooled for 3 hours.

After about one hour, the entire solution became a pseudo-solid phase, and the pseudo-solid phase α-APM crystals were dropped into a receiver equipped with a cooling coil and a stirrer and pulverized therein to form a slurry, which was further cooled. The cooling was effected from 16° C. to 7° C. in the receiver.

The slurry thus obtained was filtered and dewatered in a centrifugal separator having a diameter of 36 inches to obtain wet α-APM crystals having a water content of 30 wt. %.

The wet α-APM crystals thus obtained by the pseudo-solid phase method were dried in a small fluidizing drier at 90° C. for 30 minutes and then milled in a small centrifugal mill (5000 rpm, using 1 mm screen) to obtain an original IB bundle-like crystal powder which was identified as sample B.

Sample C

An aqueous α-APM solution was crystallized by ordinary cooling crystallization, whereupon the solution was stirred (stirring crystallization not forming a pseudo-solid phase). By centrifugation, wet α-APM crystals having a water content of 60 wt. % were obtained, and were continuously fed into a MICRON DRIER (manufactured by Hosokawa Micron Co.) via a screw feeder and air-dried therein with hot air at 140° C. to obtain an original IIA needle-like crystal powder.

40 wt. % of the thus obtained original IIA needle-like crystal powder and 60 wt. % of the previously obtained original IB needle-like crystal powder (sample A) were blended to give sample C.

Granulation

Each of samples A, B and C were shaped by compression shaping to obtain compressed flakes, which were then pulverized in a fine granulator and sieved through JIS standard sieves to obtain several groups of α-APM granules each having the grain size range shown in Table 1 below.

The dry compression shaping followed by pulverizing was conducted using a ROLLER COMPACTOR model WP90×30 (manufactured by Turbo Industrial Co.), the feed rate of the original powder in the compression shaping step was 40 g/min, the roll pressure was 50 kg/cm$^2$.G and the roll rotating speed was 12 rpm. The screen of the fine granulator as used in the pulverizing step was a 12-mesh screen (with opening of 1400 μm).

The dissolution time of the α-APM granules thus obtained was measured by the method described below. The results obtained are shown in Table 1.

The granulated products prepared from samples A, B, and C are storage stable when packaged and sealed in flexible bags made of polyethylene, nylon, a laminated package of polyethylene/aluminum foil and polyethylene coated paper.

Dissolution Time

Two liters of water were placed in a 3-liter beaker and stirred with a magnetic stirrer. The size of the stirrer used for stirring was 70 mm×15 mm and the rotation speed was set at 350 rpm using a Whatman DATAPLATE 440. The temperature of the water was maintained at 20° C. using a hot plate. 8 g of each sample were placed into the water under these conditions, and the time required for complete dissolution in the water was measured.

| Grain Size | Dissolution Time (min) | | |
| --- | --- | --- | --- |
| (μm) | A | B | C |
| 850 to 1400 | 38 | 35 | 38 |
| 500 to 850 | 25 | 24 | 27 |
| 300 to 500 | 18 | 17 | 19 |
| 180 to 300 | 11 | 9 | 12 |
| 150 to 180 | 8 | 7 | 20 |
| 100 to 150 | 15 | 10 | 36 |
| (Original Powder before Granulation) | 30 | 15 | 60 |

As can be seen from the table above, when the granulated product of the present invention has a grain size of from 100 to 500 microns, the dissolution time is particularly fast in contrast to the original powders prepared by milling using a 1 mm screen. The substantially larger crystals (1 mm screening product) have an average dissolution time of about 35 minutes for complete dissolution (30+15+60/3=35). In contrast, the granulated product in accordance with the invention having a grain size from 500 to 850 microns has an average dissolution time of 25.3 minutes for complete dissolution. The granules of the present invention at a 500–850 micron grain size dissolve about 28% faster (100−(25.3/35×100)= 27.7%) than the original powder before granulation.

When the grain size of the granulated product is in the range of 100–300 microns, the dissolution time is less than half the dissolution time required for the original powder. This decrease in dissolution time is substantial and represents and important improvement over prior granulated products. Granulated products which can be directly used in beverages and foods having the improved dissolution times of the granulated product of the present invention provide an improved and superior sweetener.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. Granules of alpha-L-aspartyl-L-phenylalanine methyl ester, wherein said granules contain IB crystals of alpha-L-aspartyl-L-phenylalanine methyl ester and consist essentially of grain sizes within the range of 100–1400 microns.

2. Granules of alpha-L-aspartyl-L-phenylalanine methyl ester containing IB crystals of alpha-L-aspartyl-L-phenylalanine methyl ester, wherein said granules are prepared by a process comprising the steps of:

(i) crystallizing alpha-L-aspartyl-L-phenylalanine methyl ester by stirring crystallization to obtain crystals (a) of alpha-L-aspartyl-L-phenylalanine methyl ester or by pseudo-solid phase cooling crystallization of alpha-L-aspartyl-L-phenylalanine methyl ester to obtain crystals (b) of alpha-L-aspartyl-L-phenylalanine methyl ester, and (ii) sieving said crystals (a) or said crystals (b) with sieves having 100 micron and 1400 micron holes therein, respectively, to obtain said sieved granules.

3. A package consisting essentially of a packaging material and granules of alpha-L-aspartyl-L-phenylalanine methyl ester, wherein said granules contain IB crystals of alpha-L-aspartyl-L-phenylalanine methyl ester and consist essentially of grain sizes within the range of 100–1400 microns.

4. The package of claim 3, wherein said package can be directly opened for dispensing said granules.

5. The package of claim 3, wherein said package comprises a sealable flexible bag.

6. The package of claim 5, wherein said package comprises a single walled bag.

7. The package of claim 5, wherein said package comprises a double walled bag.

8. The package of claim 5, wherein a plurality of said flexible bags are enclosed within a solid walled package.

9. The package of claim 3, wherein said granules have a grain size consisting essentially of 100 to 1400 microns, and wherein said granules comprise IIA crystals and IB crystals prepared by stirring crystallization of an aqueous alpha-L-aspartyl-L-phenylalanine methyl ester solution.

10. The package of claim 9, wherein said granules have a grain size consisting essentially of 100 to 850 microns.

11. The package of claim 3, wherein said granules have a grain size consisting essentially of 100 to 850 microns, and wherein said granules are IB crystals prepared by stirring crystallization of an aqueous alpha-L-aspartyl-L-phenylalanine methyl ester solution.

12. The package of claim 11, wherein said granules have a grain size consisting essentially of 100 to 500 microns.

13. The package of claim 3, wherein said granules have a grain size consisting essentially of 100 to 300 microns, and wherein said granules are IB crystals prepared by static crystallization of an aqueous alpha-L-aspartyl-L-phenylalanine methyl ester solution.

14. The package of claim 3, wherein said granules contain said IB crystals in an amount of 90 wt. % or more.

15. The package of claim 3, wherein said granules contain said IB crystals in an amount of less than 10 wt. %.

16. The package of claim 3, wherein 8.0 grams of said granules dissolve in water at 20° C. in 7–36 minutes.

17. A package consisting essentially of a packaging material and sieved granules of alpha-L-aspartyl-L-phenylalanine methyl ester containing IB crystals of alpha-L-aspartyl-L-phenylalanine methyl ester, wherein said granules are prepared by a process comprising the steps of:

(i) crystallizing alpha-L-aspartyl-L-phenylalanine methyl ester by stirring crystallization to obtain crystals (a) of alpha-L-aspartyl-L-phenylalanine methyl ester or by pseudo-solid phase cooling crystallization of alpha-L-aspartyl-L-phenylalanine methyl ester to obtain crystals (b) of alpha-L-aspartyl-L-phenylalanine methyl ester, and (ii) sieving said crystals (a) or said crystals (b) with sieves having 100 micron and 1400 micron holes therein, respectively, to obtain said sieved granules.

18. The package of claim 17, wherein said package can be directly opened for dispensing said granules.

19. The package of claim 17, wherein said package comprises a sealable flexible bag.

20. The package of claim 19, wherein said package comprises a single walled bag.

21. The package of claim 19, wherein said package comprises a double walled bag.

22. The package of claim 19, wherein a plurality of said flexible bags are enclosed within a solid walled package.

23. The package of claim 17, wherein said granules contain said IB crystals in an amount of 90 wt. % or more.

24. The package of claim 17, wherein said granules contain said IB crystals in an amount of less than 10 wt. %.

25. The package of claim 17, wherein said granules have a grain size consisting essentially of 100 to 300 microns.

26. The package of claim 17, wherein said granules have a grain size consisting essentially of 100 to 1400 microns, and wherein said granules comprise IIA crystals and IB crystals prepared by stirring crystallization of an aqueous alpha-L-aspartyl-L-phenylalanine methyl ester solution.

27. The package of claim 26, wherein said granules have a grain size consisting essentially of 100 to 850 microns.

28. The package of claim 17, wherein said granules have a grain size consisting essentially of 100 to 850 microns, and wherein said granules are IB crystals prepared by stirring crystallization of an aqueous alpha-L-aspartyl-L-phenylalanine methyl ester solution.

29. The package of claim 28, wherein said granules have a grain size consisting essentially of 100 to 500 microns.

30. The package of claim 17, wherein said granules have a grain size consisting essentially of 100 to 300 microns, and wherein said granules are IB crystals prepared by static crystallization of an aqueous alpha-L-aspartyl-L-phenylalanine methyl ester solution.

31. The package of claim 17, wherein 8.0 grams of said granules dissolve in water at 20° C. in 7–36 minutes.

* * * * *